United States Patent
Reyland et al.

(10) Patent No.: US 11,376,247 B2
(45) Date of Patent: Jul. 5, 2022

(54) TYROSINE KINASE INHIBITORS REGENERATE NON-CANCEROUS TISSUE AFTER CANCER THERAPY

(71) Applicant: THE REGENTS OF THE UNIVERSITY OF COLORADO, A BODY CORPORATE, Denver, CO (US)

(72) Inventors: Mary Reyland, Denver, CO (US); Sten Wie, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 47 days.

(21) Appl. No.: 16/619,289

(22) PCT Filed: Jun. 5, 2018

(86) PCT No.: PCT/US2018/036102
§ 371 (c)(1),
(2) Date: Dec. 4, 2019

(87) PCT Pub. No.: WO2018/226722
PCT Pub. Date: Dec. 13, 2018

(65) Prior Publication Data
US 2020/0138807 A1    May 7, 2020

Related U.S. Application Data

(60) Provisional application No. 62/515,451, filed on Jun. 5, 2017.

(51) Int. Cl.
| | |
|---|---|
| *A61K 31/496* | (2006.01) |
| *A61P 43/00* | (2006.01) |
| *A61K 31/4025* | (2006.01) |
| *A61K 31/5025* | (2006.01) |
| *A61K 31/506* | (2006.01) |

(52) U.S. Cl.
CPC ........ *A61K 31/496* (2013.01); *A61K 31/4025* (2013.01); *A61K 31/506* (2013.01); *A61K 31/5025* (2013.01); *A61P 43/00* (2018.01)

(58) Field of Classification Search
CPC .. A61P 31/496; A61P 31/506; A61P 31/5025; A61P 31/4025; A61P 43/00
See application file for complete search history.

(56) References Cited

U.S. PATENT DOCUMENTS

| 6,685,971 B2 | 2/2004 | Xu |
| 10,076,520 B2 * | 9/2018 | Reyland ............... A61P 35/00 |
| 2004/0087016 A1 | 5/2004 | Keating et al. |

OTHER PUBLICATIONS

Andras Rokusz et al., Imatinib accelerates progenitor cell-mediated liver regeneration in choline-deficient ethionine-supplemented diet-fed mice, International Journal of Experimental Pathology, 2016, 97(5), pp. 389-396.*
Oliver Christ et al., Transplantation of immunodeficient mice with chronic myeloid leukemia (CML) cells from chronic phase patients reveals a hierarchy of CD34(+) aldehyde dehydrogenase-positive cells with short- and long-term repopulating activity and transient responsiveness to imatinib mesylate in vivo.*
Ghoumari, Abdel M. et al., "Inhibition of Protein Kinase C Prevents Purkinje Cell Death But Does Not Affect Axonal Regeneration", The Journal of Neuroscience vol. 22 Issue 9, May 1, 2002, pp. 3531-3542.
Karin, Michael et al., "Reparative inflammation takes charge of tissue regeneration", Nature vol. 529 Issue. 7586, Jan. 21, 2016, pp. 307-315.
PCT, "International Search Report and Written Opinion", Application No. PCT/US2018/036102, dated Sep. 12, 2018, 6 pages.
Shah, Devron R., "Effect of Tyrosine Kinase Inhibitors on Wound Healing and Tissue Repair: Implications for Surgery in Cancer Patients", Drug Saf vol. 37, 2014, pp. 135-149.

* cited by examiner

*Primary Examiner* — Paul V Ward
(74) *Attorney, Agent, or Firm* — Dorsey & Whitney LLP

(57) ABSTRACT

Methods for inducing the regeneration of non-cancerous tissues in a cancer patient undergoing radiotherapy and/or chemotherapy using continuous administration of tyrosine kinase inhibitors for at least 90 days following a cancer treatment in the patient.

8 Claims, 8 Drawing Sheets

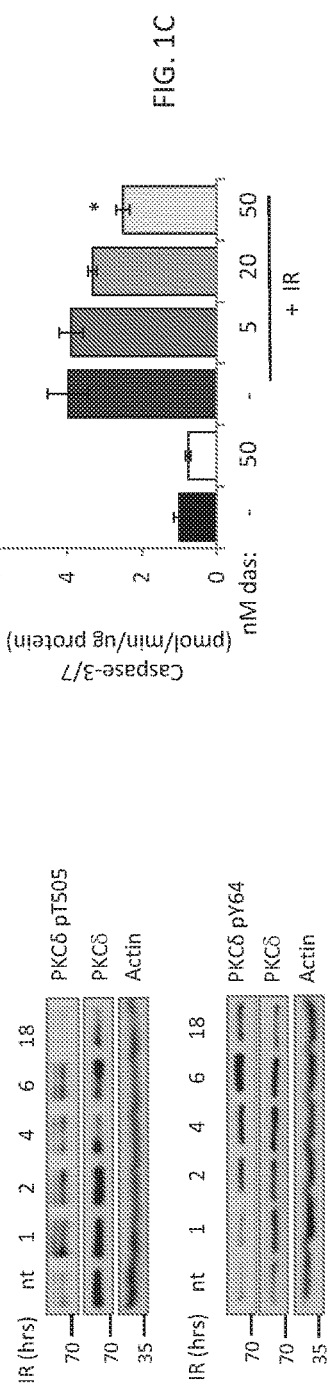
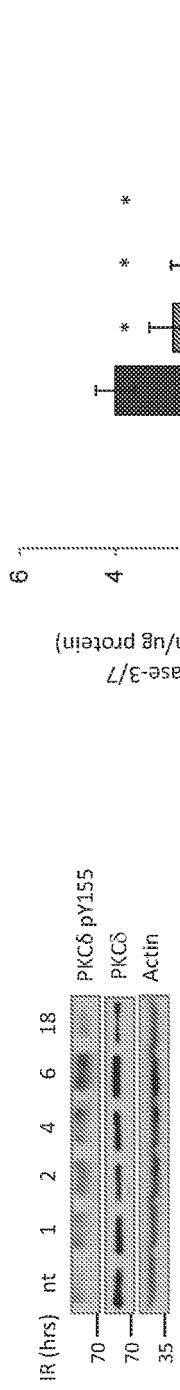
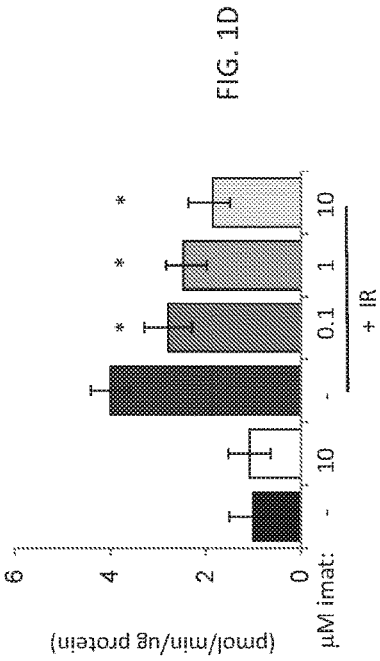
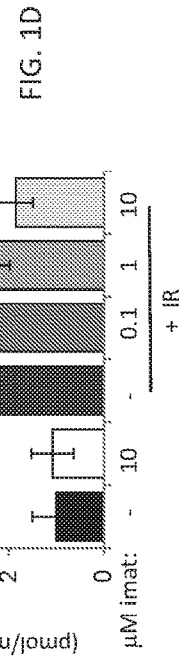
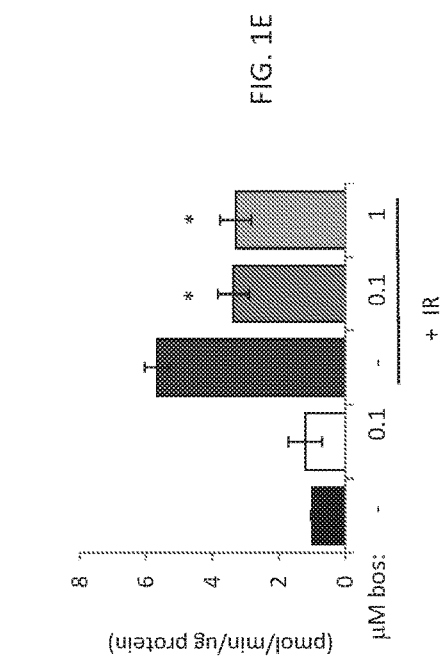
FIG. 1A
FIG. 1B
FIG. 1C
FIG. 1D
FIG. 1E

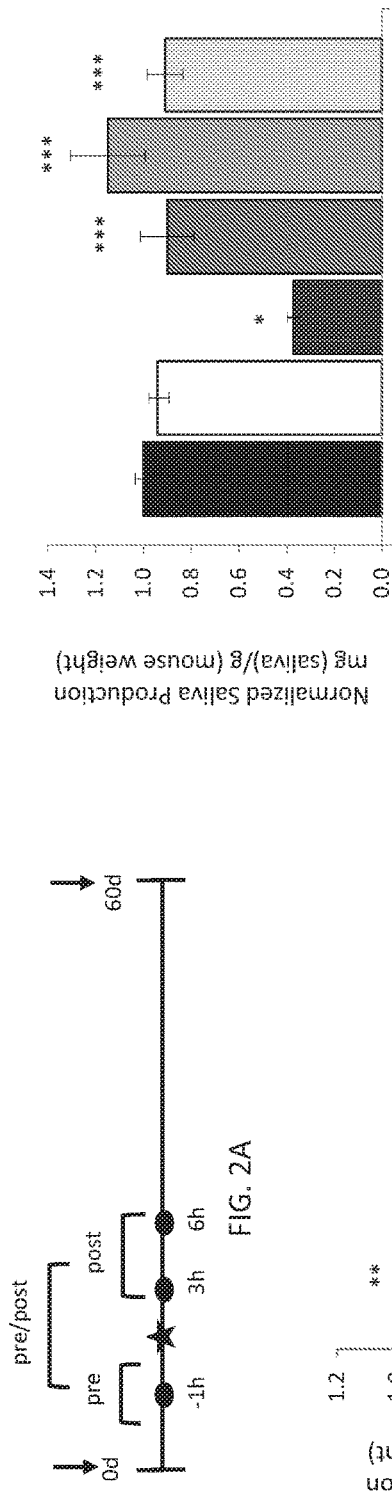
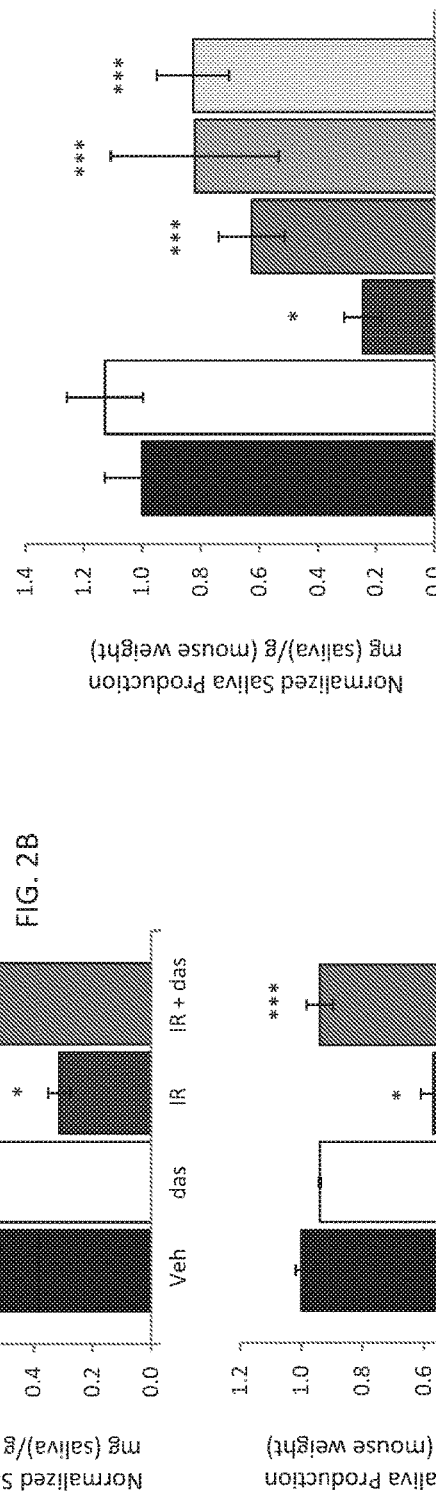
FIG. 2A, FIG. 2B, FIG. 2C, FIG. 2D, FIG. 2E

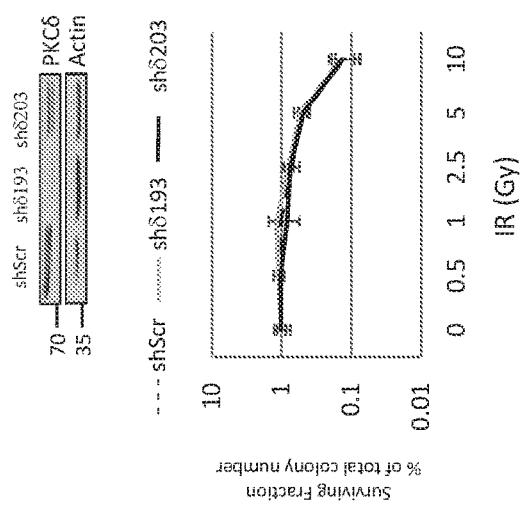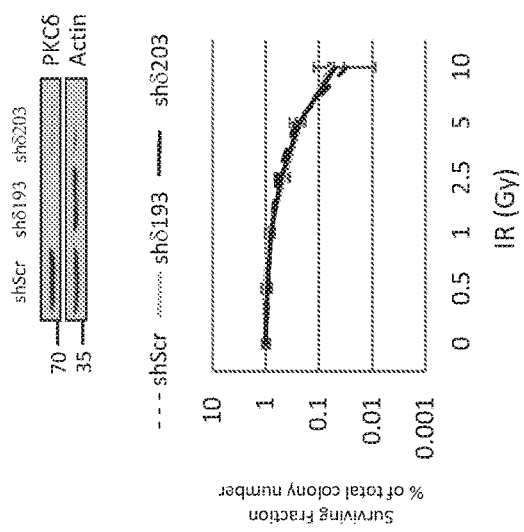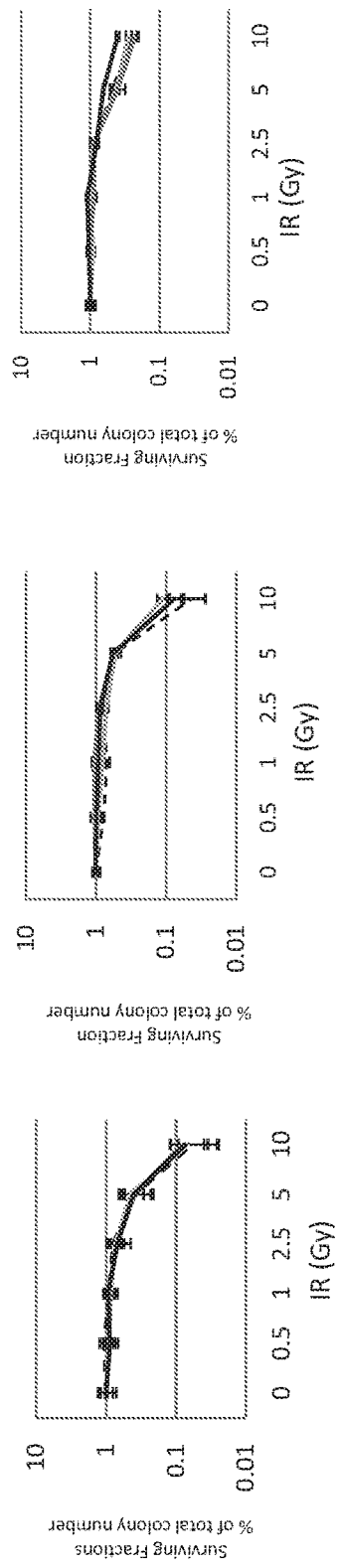
FIG. 4A  FIG. 4B  FIG. 4C  FIG. 4D  FIG. 4E  FIG. 4F

TYROSINE KINASE INHIBITORS REGENERATE NON-CANCEROUS TISSUE AFTER CANCER THERAPY

CROSS-REFERENCE TO RELATED APPLICATIONS

This application is a national stage application under 35 U.S.C. § 371 of International Application No. PCT/US2018/036102, filed Jun. 5, 2018, entitled "TYROSINE KINASE INHIBITORS REGENERATE NON-CANCEROUS TISSUE AFTER CANCER THERAPY," which claims the benefit of U.S. Provisional Patent Application Ser. No. 62/515,451, filed Jun. 5, 2017, the entire disclosures of which are hereby incorporated herein by reference.

GOVERNMENT INTEREST

This invention was made with government support under grant numbers DE015648 and DE024309 awarded by the National Institutes of Health. The U.S. government has certain rights in the invention.

TECHNICAL FIELD

The invention is directed to methods for regenerating non-cancerous tissue in a patient receiving radiation therapy or chemotherapy.

BACKGROUND

The majority of patients diagnosed with cancer will receive irradiation (IR) therapy, either alone or in combination with surgery or chemotherapy. Despite improvements in IR delivery, damage to healthy tissues and the associated morbidities can significantly impact quality of life. Furthermore, IR toxicity, especially in combination with chemotherapy, can limit the course of therapy, potentially impacting tumor eradication in some patients.

In the oral cavity, the oral mucosa and the salivary glands are highly sensitive to IR damage. Up to 40% of patients treated with IR for head and neck carcinoma (HNC) will develop moderate to severe xerostomia as a result of collateral damage to the salivary glands in the IR path. These patients typically experience a reduction in saliva production of >50% within a few weeks of commencing therapy. Salivary gland hypofunction, and the resultant xerostomia, is often permanent and can have a significant impact on oral health and nutrition. Currently, the only therapeutic agent available to protect the salivary gland is the free radical scavenger, amifostine, which is not widely used due to significant toxicity. Thus, there is a need for the development of new therapeutic strategies that will provide selective protection of these radiosensitive normal tissues without impacting tumor cell death.

SUMMARY

The inventors have surprising discovered that administration of a tyrosine kinase inhibitor (TKI) can induce regeneration of non-cancerous tissue injured or killed by a cancer treatment, such as radiation therapy (IR) or chemotherapy, if the TKI is administered continuously to the cancer patient and for at least 10 days, at least 20 days, at least 30 days, at least 40 days, at least 50 days, at least 60 days, at least 70 days, at least 80 days, or at least 90 days, or more following administration of the cancer treatment. These methods are particularly suited to regeneration of salivary gland acinar cells following radiation therapy in a cancer patient. In these methods, the TKIs are useful to regenerate non-tumor tissue, such as salivary gland acinar cells, in cancer patients undergoing radiation therapy without negatively impacting the cancer therapy.

Therefore, one aspect of this disclosure is a method for regenerating non-cancerous cells following a cancer treatment, by administering a therapeutically effective amount of a tyrosine kinase inhibitor (TKI) for several months after administering a cancer treatment to a cancer patient.

In a related aspect, this disclosure provides a method for treating a cancer patient, by administering a tyrosine kinase inhibitor (TKI) to a cancer patient prior to administering a cancer treatment and thereafter continuously administering the TKI to the patient for at least 10-300 days, or for at least 40-250 days, or for at least 70-200 days, or for at least 90-150 days following the administration of the cancer treatment.

In a related aspect, this disclosure provides a method for regenerating non-cancer tissues in a cancer patient, by administering a tyrosine kinase inhibitor (TKI) to a cancer patient prior to administering a cancer treatment and thereafter continuously administering the TKI to the patient for at least 90-150 days following the administration of the cancer treatment.

In any of these aspects, the cancer treatment may comprise radiation therapy.

In any of these aspects, the cancer treatment may comprise chemotherapy.

In any of these aspects, the TKI may be an inhibitor of at least one of Protein Kinase C-delta, c-Abl-, and Src-family kinase.

In any of these aspects, the TKI may be an inhibitor of at least one non-receptor tyrosine kinase.

In any of these aspects, the TKI may be selected from bosutinib, dasatinib, imatinib, nilotinib, pazopanib, ponatinib, sunitinib, and combinations thereof.

In any of these aspects, the cancer may be head and neck cancer, pancreatic cancer, stomach cancer, breast cancer, colon cancer, lung cancer, liver cancer, leukemia, bone cancer, ovarian cancer, cervical cancer, brain cancer, skin cancer, prostate cancer, or thyroid cancer.

In any of these aspects, the TKI may be administered once weekly, or at least twice weekly, or at least 3, 4, 5, 6, or 7 times weekly, or more, following the administration of the cancer treatment.

In any of these aspects, the TKI may be administered continuously for at least 90-150 days following the administration of the cancer treatment.

BRIEF DESCRIPTION OF THE DRAWINGS

FIGS. 1A-1H demonstrate that tyrosine kinase inhibitors suppress tyrosine phosphorylation of Protein Kinase C-delta (PKC-delta) and IR induced apoptosis in salivary gland acinar cells. FIG. 1A shows ParC5 cells treated with 10 Gy IR and collected at the indicated time after IR. Whole cell lysates were resolved with SDS-PAGE and analyzed using phospho-specific antibodies that recognize PKC-delta pY64, pY155 or pT505. Membranes were stripped and probed for total PKC-delta and actin to determine loading. Each experiment was done a minimum of three times; representative immunoblots are shown. FIG. 1B shows ParC5 cells transiently infected with lentivirus expressing PKC-delta specific shRNAs (sh-delta1 or sh-delta3) or a scrambled control shRNA (shScr), after 72 hours treated with IR (10Gy), and harvested after an additional 18 hr. Caspase-3/7 activity was assayed as described in the Examples. Data shown is the average of triplicate samples from a representative experiment plus and minus the S.D. (error bars). The experiment was repeated three times, *=p<0.05 for caspase activity compared to cells expressing shScr. An immunoblot showing depletion of PKC-delta is shown below. For FIGS. 1C-1H: ParC5 cells were treated with increasing concentrations of dasatinib (FIG. 1C, FIG. 1F), imatinib (FIG. 1D, FIG. 1G), or bosutinib (FIG. 1E, FIG. 1H) for 30 min, followed by treatment with 10 Gy IR (FIG. 1C-FIG. 1E), or the addition of 5 mM H2O2 for 30 min (FIG. 1F-FIG. 1H). FIGS. 1C-1E shows lysates collected for caspase-3/7 activity analysis 18 hours after IR and assayed as described in the Examples. The data are the average of triplicate measurements from a representative experiment plus the S.D. (error bars). Each experiment was repeated three times. *=p<0.05 for caspase activity compared to cells treated with IR alone. FIGS. 1F-1H shows whole cell lysates collected 30 minutes after H2O2 treatment and analyzed by immunoblot for PKC-delta pY64 and pY155. Inhibition of c-Src and c-Abl was determined by probing for their respective activation sites pY416 (c-Src) and pY412 (c-Abl). Blots were stripped and probed for total PKC-delta, total SFK, total c-Abl and actin to determine total protein levels and loading efficiency. Experiments were done a minimum of three times; representative immunoblots are shown.

FIGS. 2A-2E demonstrate that treatment with TKIs protects against IR induced salivary gland damage. FIG. 2A shows experimental design of the experiments shown in FIGS. 2B-2E. The star indicates time of IR treatment. Three TKI dosing regimens were used, where times of delivery is indicated by the filled circles. Mice were treated with the specific TKI 1 hour prior to delivery of IR (pre), 1 hour prior and 3 hours post IR (pre/post), or 3 and 6 hours post (post/post). Saliva production was assayed prior to IR (day 0) and at 60 days after IR as described in Examples. FIGS. 2B-2C show mice that received vehicle alone (Veh), 15 Gy (B) or 10 Gy (C) IR plus vehicle, IR plus pre/post dosing of dasatinib (20 mg/kg) (FIG. 2B) or imatinib (50 mg/kg) or TKI alone. FIGS. 2D-2E show mice that received vehicle, or IR plus dasatinib (FIG. 2D), imatinib (FIG. 2E) or vehicle using pre, pre/post, or post/post regimens. Saliva was collected i.p. as described in Examples. Salivary production (saliva weight/animal weight) for each cohort of mice was normalized against the saliva production for vehicle treated mice to generate the data shown. Data shown represents the average plus the S.E.M. (error bars) (n>3). *=p<0.05 saliva collected from mice which received IR alone compared to the vehicle treated mice. =p<0.001 saliva collected from mice treated with vehicle compared to mice that received IR plus TKI treatment. *=p<0.05 saliva collected from mice treated with IR alone compared to mice that received TKI treatment with IR.

FIG. 3A shows experimental design of pre/post and continuous dosing protocols. The star indicates time of IR treatment; while TKI delivery is indicated by the filled circles and arrows indicate time of saliva collection. Mice were dosed 1 hour prior and 3 hours post IR (pre/post), or pre/post plus twice a week for the duration of the experiment. Saliva production was assayed prior to IR (day 0) and at 30, 60, 90, 120 and 150 days after IR. Mice received vehicle alone, 15 Gy IR plus vehicle, or IR plus dasatinib as indicated. Saliva production (saliva weight/animal weight) for each cohort of mice was normalized against the production for vehicle-treated mice to generate the data shown in FIG. 3B. Data represents the average plus the S.E.M. (error bars) (n>3). *=p<0.01 saliva collected from mice treated with IR compared to vehicle mice. ***=p<0.05 saliva collected from mice treated with IR alone compared to mice that received TKI treatment with IR. Salivary glands from mice in each group (n=2) were removed, formalin fixed and paraffin embedded. Immunohistochemistry for AQPN5 and H&E staining was performed on salivary glands from each mouse. FIG. 3C shows representative images (20×) of the SMG in each treatment group, scale=200 micrometers. Images were captured using an Olympus BX51 scope and Olympus DP72 camera with a 20× objective. Solid arrows indicate acinar cells while dashed arrows mark salivary gland ducts. In FIG. 3D, data is shown that represents the average number of AQPN5 positive pixels plus the standard deviation (error bars) from three full representative sections of both SMG from two mice per treatment group. *=p<0.0001 number of pixels in IR treated or pre/post treated mice compared to vehicle treated mice. ***=p<0.0001 number of pixels in IR treated mice compared to mice that received IR and continuous dasatinib treatment.

FIGS. 4A-4I demonstrate that depletion of PKC-delta or treatment with TKIs does not enhance survival of HNSCC cells. Ca127 (FIG. 4A), FaDu (FIG. 4B), or UMSCC19 (FIG. 4C) HNSCC cells were stably transduced with lentivirus to express PKC-delta-specific shRNAs (sh-delta193 and sh-delta203) or a scrambled control (shScr). An immunoblot showing depletion of PKC-delta is shown above. 24 hours after plating, cells were exposed to IR (0-10Gy). Ca127 (FIG. 4D), FaDu (FIG. 4E), and UMSCC19 (FIG. 4F) cells were plated, and 24 hours later were treated with DMSO (vehicle), dasatinib (50 nM), imatinib (10 micromolar), or bosutinib (1 micromolar) for 30 min prior to IR (0-10 Gy). Colonies were allowed to form over 10-14 days. The plating efficiency and surviving fractions from each condition were quantified using Image J as described in Examples. The data represents the average plating efficiency from three independent experiments plus the standard deviation (error bars). Ca127 (FIG. 4G), FaDu (FIG. 4H), and UMSCC19 (FIG. 4I) cells were treated with DMSO (Veh), 50 nM dasatinib alone (Das), or 10 Gy IR alone (IR), or given 50 nM dasatinib 30 min prior to 10 Gy IR (D+IR); cells were harvested 1 hour after IR. Whole cell lysates were analyzed for phospho-Akt and phospho-ERK, and stripped and probed for total Akt, total ERK, and actin. Shown are representative images from one experiment that was repeated three or more times.

DETAILED DESCRIPTION

Figures 1F, 1G, 1H:
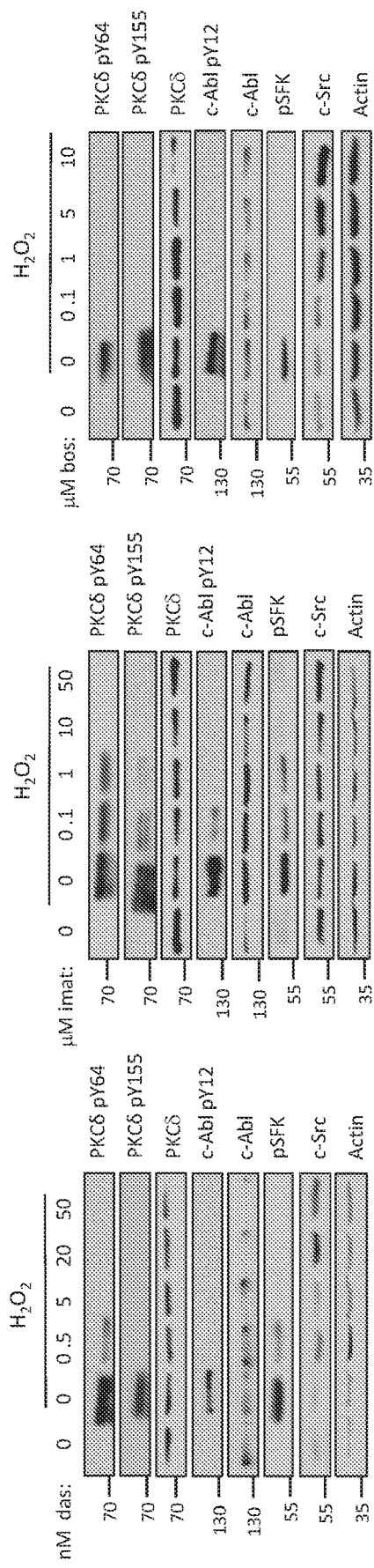

The present invention pertains to the surprising discovery that administration of tyrosine kinase inhibitors (TKIs) to a cancer patient for several months after the administration of radiation therapy can induce the regeneration of salivary gland acinar cells.

While most damage to non-tumor tissues in the oral cavity resolves in the months following irradiation (IR), damage to the salivary gland, and the resulting xerostomia ("dry mouth syndrome") can be permanent, particularly for those patients with locally advanced head and neck cancer (HNC). Considerable effort has been put into restoring the function of IR damaged glands by gene transfer of AQPN5 into residual ductal cells, or implantation of autologous, cryopreserved salivary gland tissue harvested from the patient before radiation/chemotherapy (Baum B J, et al. Early responses to adenoviral-mediated transfer of the aquaporin-1 cDNA for radiation-induced salivary hypofunction. Proc Natl Acad Sci USA. 2012 Nov. 20; 109(47):19403-7; Ogawa M, et al. Functional salivary gland regeneration by transplantation of a bioengineered organ germ. Nature Communications. 2013 Oct. 1; 4:2498), and both of these approaches show remarkable promise for patients who suffer from severe loss of salivary gland function. But the inventors' findings provide a safer, less invasive, and more cost-effective therapy to regenerate salivary glands following damage due to cancer therapy, including radiation therapy, alone or in conjunction with chemotherapy.

Therefore, this disclosure provides methods for regenerating non-cancerous cells following a cancer treatment. These methods comprise administering a therapeutically effective amount of a tyrosine kinase inhibitor (TKI) following the administration of a cancer treatment to a cancer patient. As used herein, the term "regenerating non-cancerous cells" refers to regenerating at least 30%, at least 60%, at least 80%, or at least 90% of non-cancerous cells using the methods of this disclosure. In these methods, the TKI is administered to the cancer patient at least twice weekly for at least 90-150 days following the administration of the cancer treatment to the patient.

These methods may include the administration of a second TKI after administering the cancer treatment to the cancer patient. The second TKI can be the same as the TKI that is administered prior to cancer treatment or it can be a different TKI. Typically, the same TKI is used pre- and post-cancer treatment. When a TKI is administered after cancer treatment, typically it is administered for at least 90 days, and more often for at least 150 days after a cancer treatment.

In these methods, the administration of the tyrosine kinase inhibitor continuously for at least 90-150 days following the cancer treatment induces regeneration of non-cancerous cells injured or killed by the cancer treatment.

In these methods, the non-cancerous tissue that may be regenerated following radiotherapy or chemotherapy may be salivary gland acinar cells.

In these methods, the cancer treatment may comprise radiotherapy, chemotherapy, or a combination of radiotherapy and chemotherapy.

In these methods, the tyrosine kinase inhibitor may inhibit one or more of Protein kinase C (PKC-delta), c-Abl, and Src-family kinases.

Tyrosine kinase inhibitors that may be useful in methods of this disclosure include, but are not limited to, bosutinib, dasatinib, imatinib, nilotinib, pazopanib, ponatinib, sunitinib, and combinations thereof.

Non-receptor tyrosine kinases (nRTKs) are cytoplasmic enzymes that are responsible for catalyzing the transfer of a phosphate group from a nucleoside triphosphate donor, such as ATP, to tyrosine residues in proteins. Non-receptor tyrosine kinases are a subgroup of protein family tyrosine kinases. These enzymes can transfer the phosphate group from ATP to a tyrosine residue of a protein (phosphorylation). These enzymes may regulate many cellular functions by switching on or switching off other enzymes in a cell. Unlike the receptor tyrosine kinases (RTKs), this second subgroup of tyrosine kinases (the non-receptor tyrosine kinases) are cytoplasmic enzymes. Thirty-two non-receptor tyrosine kinases have been identified in human cells (EC 2.7.10.2). Non-receptor tyrosine kinases regulate cell growth, proliferation, differentiation, adhesion, migration and apoptosis, and they are believed to be components involved in the regulation of the immune system. Exemplary Non-receptor tyrosine kinases that may be inhibited in the methods of this disclosure include members of the ABL family (ABL1, ARG), or the ACK family (ACK1, TNK1), or the CSK family (CSK, MATK), or the FAK family (FAK, PYK2), or the FES family (FES, FER), or the FRK family (FRK, BRK, SRMS), or the JAK family (JAK1, JAK2, JAK3, TYK2), or the SRC family (SRC, FGR, FYN, YES1, BLK, HCK, LCK, LYN), or the TEC family (TEC, BMX, BTK, ITK, TXK), or the SYK family (SYK, ZAP70). Thus, in the methods of this disclosure the tyrosine kinase inhibitor may inhibit one or more non-receptor tyrosine kinases. The tyrosine kinase inhibitor may specifically inhibit a non-receptor tyrosine kinase. Exemplary non-receptor tyrosine kinase inhibitors useful in the methods of this disclosure include bosutinib, dasatinib, imatinib, nilotinib, pazopanib, ponatinib, sunitinib, and combinations thereof.

Exemplary cancers for which methods of this disclosure are useful include, but are not limited to, head and neck cancer, pancreatic cancer, stomach cancer, breast cancer, colon cancer, lung cancer, liver cancer, leukemia, bone cancer, ovarian cancer, cervical cancer, brain cancer, skin cancer, prostate cancer, and thyroid cancer.

Other aspects of the invention include methods for treating a cancer patient. Such methods include administering a tyrosine kinase inhibitor to a cancer patient continuously following a cancer treatment to regenerate non-cancerous cells that were injured or killed by the cancer treatment.

Typically, the tyrosine kinase is administered to the cancer patient for at least 90-150 days following the administration of the cancer treatment.

Typically, the TKI is administered in formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The TKI may be administered by direct injection at or near the site of radio- or chemo-therapy.

Additional objects, advantages, and novel features of this invention will become apparent to those skilled in the art upon examination of the following examples thereof, which are not intended to be limiting.

EXAMPLES

Data analysis for all studies described in the following examples consisted of data analyzed in Excel or in Graph Pad Prism 6. Shapiro-Wilk tests for normalcy were applied, and if data were determined to be abnormally distributed, nonparametric analyses were performed. Otherwise, parametric statistical analysis was performed (t-tests, ANOVA). Graphical data are presented as mean+SEM unless otherwise noted.

Example 1

PKC-Delta is Activated in Response to IR and is Required for IR-Induced Apoptosis in Salivary Gland Acinar Cells We previously demonstrated that PKC-delta−/− mice are resistant to IR-induced damage to the salivary gland and thymus and have a delay in mammary gland involution, a process driven by apoptosis (Humphries Mi, et al., *Suppression of apoptosis in the protein kinase Cdelta null mouse in vivo.* J Biol Chem. 2006 Apr. 7; 281(14):9728-37; Allen-Petersen B L, et al., *Loss of protein kinase C delta alters mammary gland development and apoptosis.* Cell Death Dis. 2010; 1(1):e17). Our studies demonstrated that phosphorylation of PKC-delta at Y64 and Y155 by cSrc and c-Abl, respectively, drives nuclear translocation, and is necessary and sufficient for the pro-apoptotic function of PKC-delta.

To determine if PKC-delta is activated in response to IR, we examined phosphorylation of PKC-delta at T505 in the activation loop of the kinase, and at Y64 and Y155 in the regulatory domain.

ParC5 cells were transduced with lentivirus to transiently or stably express a non-specific "scrambled" shRNA (shScr) (Open Biosystems, Pittsburgh, Pa., USA #RHS4080) or rat PKC-delta specific shRNAs (shdl and shd3) (Open Biosystems, #RMM433198725640 and RMM4331-99343143). For stable expression, cells were maintained in media with 2 microgram/mL puromycin. HNSCC cells were stably transduced with lentiviruses that express an shRNA targeting human PKC-delta (sh-delta193 and sh-delta193) (Open biosystems), or a non-targeting "scrambled" shRNA (shScr). Cells were maintained in media with 2 microgram/mL puromycin.

Phosphorylation of PKC-delta at T505 is seen within 1 hour after IR, while phosphorylation at Y64 and Y155 are detectable by 2 hours post IR and continue to increase until at least 6 hours (FIG. 1A). To determine if PKC-delta is required for IR-induced apoptosis, we assayed caspase activation in cells depleted of PKC-delta with specific shRNAs (shdl and shd3) or a scrambled shRNA (shScr). Active caspase-3/7 was detected using the Caspase-3/7 Cellular Activity Assay Kit PLUS (Biomol, Farmingdale, N.Y.) according to the manufacturer's instructions. Expression of sh-delta3 reduced apoptosis by up to 50% relative to cells transfected with a scrambled shRNA control, and a similar trend was seen with sh-delta1 (FIG. 1B).

Example 2

TKIs Block Activation of PKC d and Suppress Apoptosis

We have previously shown that both dasatinib and imatinib can block phosphorylation of PKC-delta at Y64 and Y155, nuclear translocation of PKC-delta, and apoptosis in response to DNA damaging agents (Wie S M, et al., *Inhibiting Tyrosine Phosphorylation of Protein Kinase Cδ (PKCδ) Protects the Salivary Gland from Radiation Damage.* J Biol Chem. 2014 Feb. 25:jbc.M114.551366). We have now discovered that pretreatment of ParC5 cells with dasatinib, imatinib, or bosutinib, all of which target c-Src and/or c-Abl, inhibits IR-induced apoptosis (FIGS. 1C-1E). IR-induced apoptosis was reduced 40 60% by all TKIs, with bosutinib and imatinib being more potent than dasatinib. Likewise, activation of c-Abl and c-Src (SFK, Src family kinases) and phosphorylation of PKC-delta at Y155 and Y64 were also suppressed by pretreatment with TKIs (FIGS. 1F-1H). Interestingly, dasatinib and imatinib were slightly more potent inhibitors of Y155 phosphorylation than Y64 phosphorylation, consistent with their more potent inhibition of c-Abl than c-Src in ParC5 cells (FIGS. 1F and 1G).

Example 3

TKIs Protect Salivary Gland Function in Mice Treated with Head and Neck IR

To explore radioprotection by TKIs in vivo we focused on dasatinib, a broad spectrum TKI, and imatinib, which preferentially inhibits c-Abl tyrosine kinase. The schematic in FIG. 2A depicts the 3 dosing regimens used for the experiments in FIG. 2. To determine if dasatinib (FIG. 2B) or imatinib (FIG. 2C) can protect salivary gland function, mice were dosed 1 hour before and 3 hours following IR delivery ("pre/post") and production of whole saliva was assayed after 60 days.

C57Bl/6 and athymic nude female mice were purchased from Jackson Laboratories (Bar Harbor, Me., USA). For single dose IR, mice were anesthetized by intraperitoneal (i.p.) injection of 0.1 mg/kg Avertin (Sigma), immobilized within a 50-mL conical tube, and a single dose of IR (10 or 15 Gy) was delivered to the head and neck using a Caesium-137 source. For fractionated IR, mice received 5 fractions of 6 Gy (tumor study) or 4 Gy (saliva production) on 5 consecutive days. Imatinib (50 mg/kg) and dasatinib (20 mg/kg) were given to mice via oral gavage at the indicated times. Control mice for imatinib and dasatinib were gavaged with water or citric acid buffer pH 2.1, respectively.

Saliva was collected immediately following i.p. injection of 0.1 mg/kg carbachol (Sigma) in saline (0.9% NaCl). Whole saliva was collected for 3 mins from the lower cheek pouch using a suction device and expressed as mg (saliva)/g (mouse weight).

For tissue analysis, salivary glands were formalin fixed, paraffin embedded, and sectioned at 5 micromolar. Tissue sections were stained with haematoxylin-eosin (H&E) and aquaporin 5 (AQPN5) was detected by immunohistochemistry (Abcam). Stained slides were archived and analyzed using the Aperio Digital Pathology System and ImageScope software (Leica Biosystems). For AQPN5, the number of positive stained pixels was quantified using the Positive Pixel algorithm in three representative sections, cut 50 micrometers apart, of both full submandibular salivary glands from two mice per treatment group, for a total of 6 measurements per group.

Immunoblotting was done as previously described (Wie S M, et al, supra). Antibodies to PKC-delta (sc-937 and sc-213), PKC-delta pY155 (sc-233770-R) and c-Abl (sc-23) were purchased from (Santa Cruz Biotechnology, Dallas, Tex.); anti-PKC-delta pY64 was purchased from Assay Biotech, (Sunnyvale, Calif., USA). Antibodies against Src pY416, Src family kinases (SFK), Akt pS473, Akt, ERK 44/42 pT202/pY204 and ERK, were purchased from (Cell Signaling, Beverley, M A). Anti-c-Abl pY412 was purchased from Novus Biological (Littleton, Colo.). The anti-actin antibody was purchased from (Abcam, Cambridge, England).

While whole saliva includes secretions from the 3 major salivary glands (submandibular, parotid and sublingual), the majority is produced by the submandibular glands (SMG). In mice that received IR plus vehicle, the saliva production was significantly reduced at 60 days post IR, reaching only 30% of the vehicle treated mice (FIG. 2B). Dasatinib administration partially prevented the IR-mediated decrease in saliva production, and these mice produced 65% of the vehicle treated controls (FIG. 2B). Salivary gland function was protected to even a greater extent in mice treated with imatinib in conjunction with IR (FIG. 2C); these mice retained >90% of their salivary function when treated with imatinib plus IR compared to IR alone.

We next asked if treatment with a single dose of dasatinib or imatinib prior to IR is sufficient for radioprotection (see FIG. 2A "pre"), and if delivery of dasatinib or imatinib after IR affords radioprotection (see FIG. 2A "post/post"). In the experiment shown in FIG. 2D, saliva production after IR treatment was reduced by 70%. Remarkably, a single dose of dasatinib given prior to IR (pre), or 2 doses of dasatinib given post IR (post/post), offered similar protection as dosing mice pre/post IR (FIG. 2D). All 3 treatment protocols with dasatinib resulted in nearly 100% protection of salivary gland function compared to vehicle only treated mice (FIG. 2D). Similar results were seen in mice treated with imatinib (FIG. 2E). Salivary gland function was >80% of the vehicle control with pre/post or post/post-delivery of imatinib, while one dose prior to IR (pre) resulted in saliva production 63% of the vehicle control (FIG. 2E).

Figure 3A:
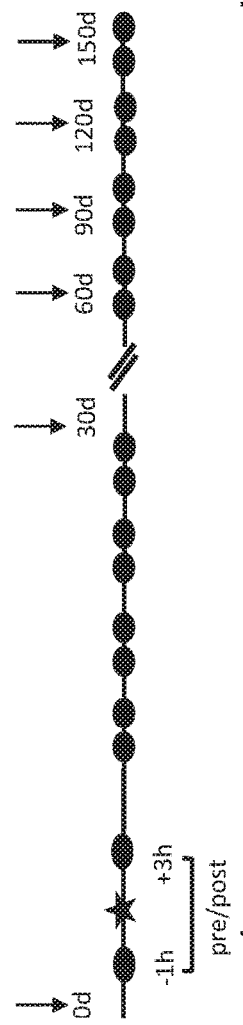
FIGS. 3A-3D demonstrate that continuous treatment with dasatinib results in durable protection of salivary gland function.

In patients, decreased salivary gland function is seen in the first weeks after IR and is presumably due to apoptosis of IR-damaged cells. In contrast, the inability to regenerate new salivary acinar cells presumably contributes to the permanent salivary gland hypofunction seen in many patients. Our studies demonstrate that dasatinib and imatinib can provide robust protection of salivary gland function for at least 60 days after delivery of IR. To address whether radioprotection persists beyond this time, we compared the effect of IR on saliva production in mice that received the pre/post treatment alone to mice that received the pre/post regimen and then continued to receive dasatinib twice a week for up to 5 months following a single dose of IR (see FIG. 3A for scheme).

Figure 3B:
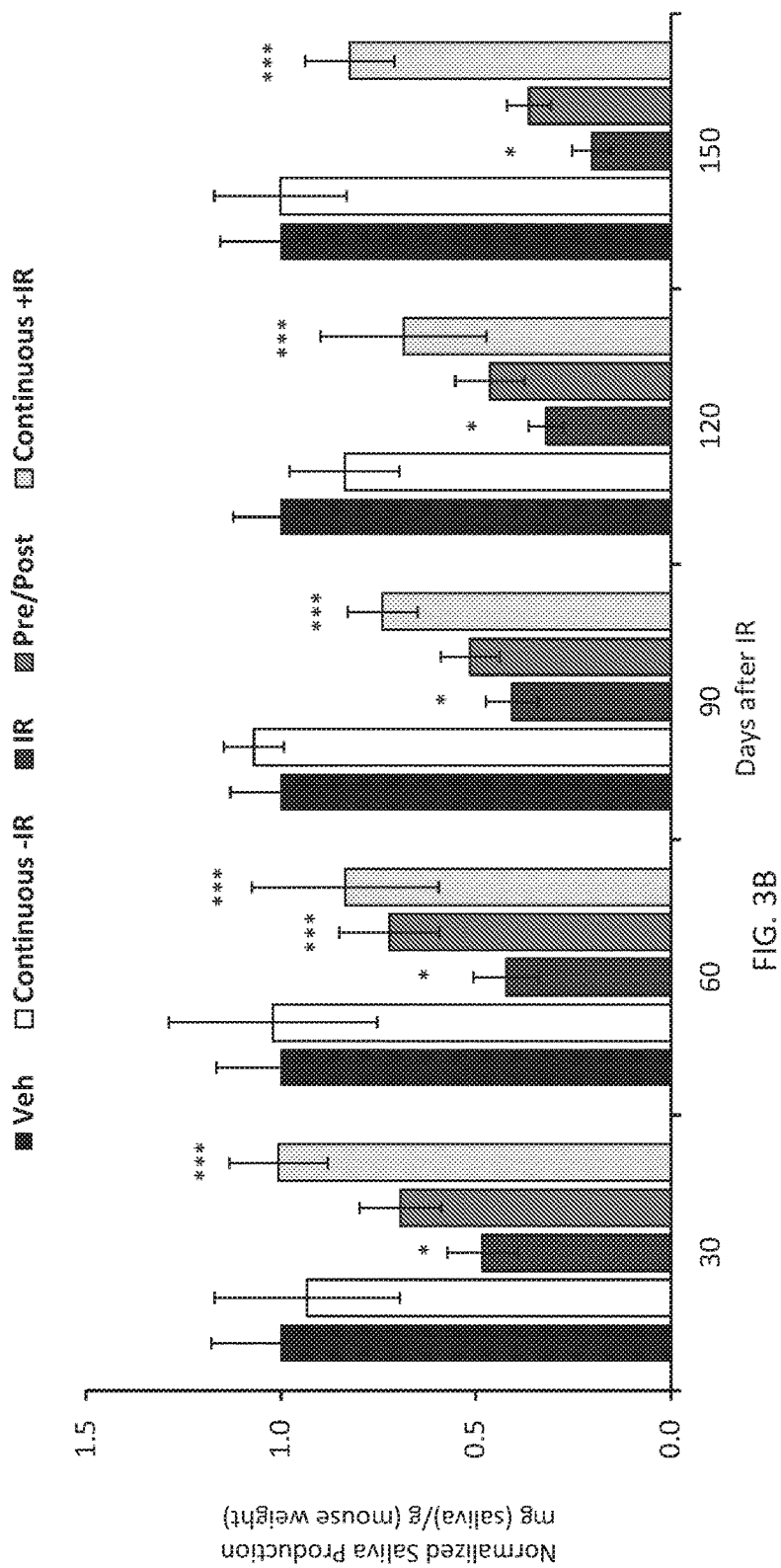

As seen in FIG. 3B, salivary function in mice that received IR alone was 50% of vehicle treated mice at 30 days, and decreased to 20% at 150 days. In comparison, in mice dosed only before and after IR (pre/post), saliva production at 30 and 60 days were 70% of vehicle treated mice, but declined thereafter (FIG. 3B). Saliva production in this group were not significantly different from IR alone at 90, and 120 days. In contrast, mice that received continual dosing with dasatinib maintained a significantly higher level of salivary function out to 5 months. In this group, saliva production was 74% of vehicle treated controls at 90 days, 69% at 120 days, and 82% at 150 days after IR (FIG. 3B).

Protection of salivary gland function in mice treated with dasatinib plus IR is suggestive of salivary gland tissue preservation, and/or increased gland regeneration. To ask if increased saliva production correlates with an increase in salivary acinar cell number, the experiment shown in FIG. 3B was terminated after 150 days and the salivary glands were analyzed histologically.

Figure 3C:
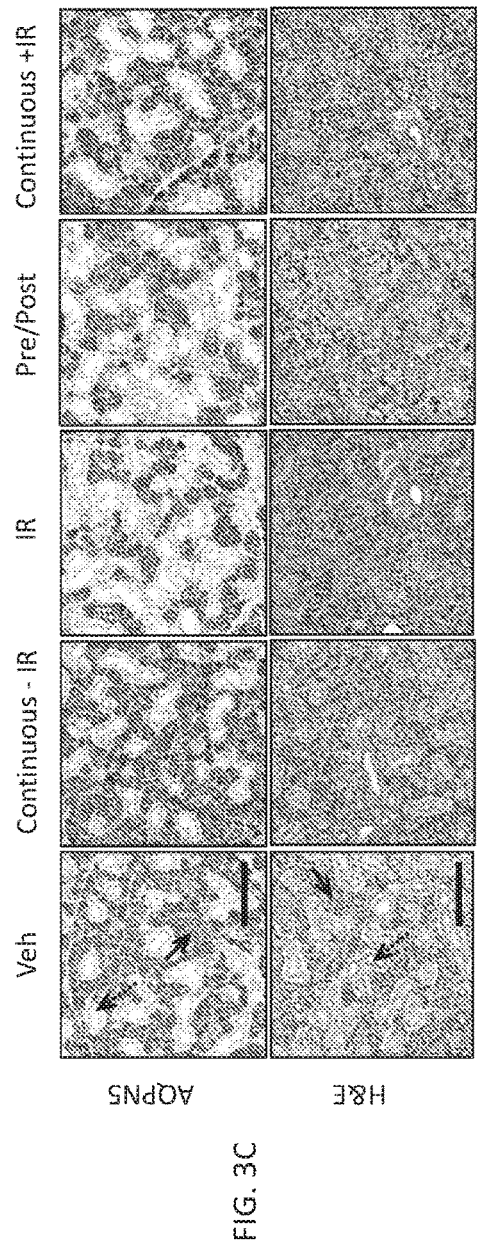

Staining with H&E revealed a decrease in salivary gland acinar cells in the SMGs of mice treated with IR alone, however this appeared to be largely reversed in mice that received continuous dosing with dasatinib (FIG. 3C). To quantify the saliva-producing acinar cells, tissue sections from the entire salivary gland were stained by immunohistochemistry for expression of aquaporin 5 (AQPN5), a specific acinar cell marker, and the relative expression of AQPN5 across different treatment groups was quantified using Aperio Image Analysis software.

Figure 3D:
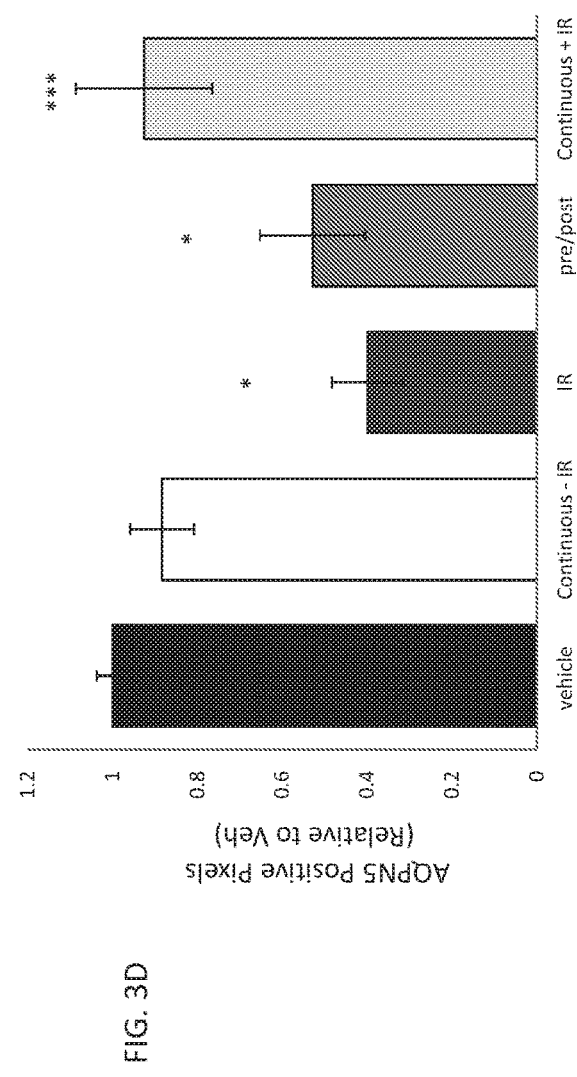

In IR-treated mice, the SMG acinar cell population was reduced by 60% compared to the SMGs of un-irradiated mice (FIGS. 3C-3D). This correlates with the 80% decrease in saliva production we reported in the IR alone treated mice (FIG. 3B). Dasatinib treatment pre/post IR was not sufficient to prevent the decrease in acinar cells, consistent with our finding that in this treatment group saliva production was not different from the IR alone group at 150 days (FIG. 3B). However, in IR-treated mice continuously treated with dasatinib, the amount of AQPN5 staining in the SMGs was 93% of that observed in vehicle treated mice, and consistent with protection of salivary gland function in this treatment group (FIG. 3B).

Example 4

Inhibition of PKC-Delta or Treatment with TKIs does not Promote Survival of HNSCC Cells To be of benefit to patients, strategies to protect radio-sensitive non-tumor tissues must not impact tumor eradication. To address this, we examined clonogenic survival and activation of cell survival pathways in Ca127, FaDu, and UMSCC19 HNSCC cell lines stably depleted of PKC-delta, and in the context of TKI pre-treatment.

Cells expressing shScr or PKC-delta specific shRNAs were plated at 500 (ParC5) or 100 (Ca127, FaDu, UMSCC19) cells per well in triplicate. Cells were treated with IR 24 hours after plating; for some experiments cells were treated with TKIs 30 minutes prior to IR. Media was replaced with media without TKIs 24 hours post IR. After 7-14 days, cells were fixed and stained with 0.5% crystal violet (Fisher Scientific, #C581-25) in −20° C. methanol (Fisher Scientific, #A454-4) on ice, and colony number was quantified using Image J software. Data is graphed such that the number of colonies at 0 Gy represents the plating efficiency (PF=Average number of colonies/cells plated) and the surviving fraction represents the colony number for each dose of IR (SF=Average number of colonies/PE).

Figures 4G, 4H, 4I:
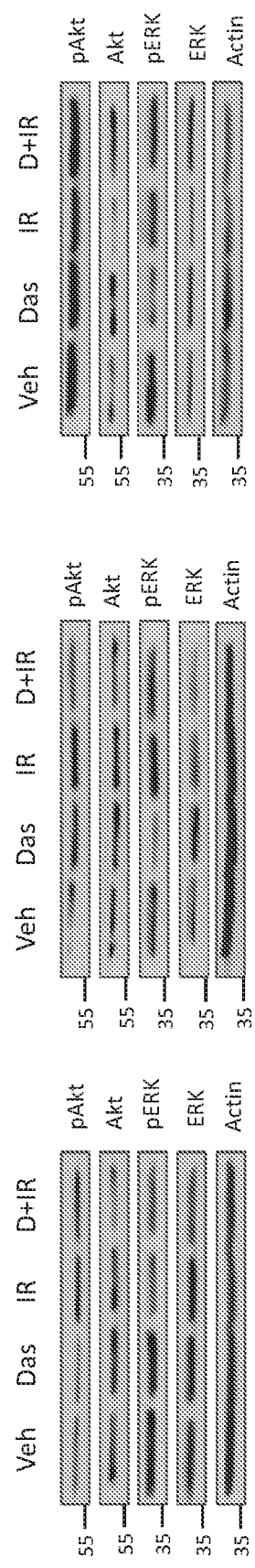

Depletion of PKC-delta had no impact on the clonogenic survival of any of the HNSCC cell lines analyzed (FIGS. 4A-4C). Basal activation of the pro-survival pathways, Akt (pAkt) or ERK (pERK) was also not altered with depletion of PKC-delta. Similarly, there was no change in clonogenic survival following IR of Ca127, FaDu, or UMSCC19 cells treated with dasatinib, imatinib, or bosutinib (FIGS. 4D-4F). To confirm that TKI treatment does not affect pro-survival signaling, Ca127, FaDu, and UMSCC19 cells were treated with dasatinib, IR, or dasatinib plus IR. As seen in FIGS. 4G-4I, while IR resulted in a modest increase in pAkt and/or pERK in Ca127 and FaDu cells, the addition of dasatinib had no effect, or reduced the level of activation.

Example 5

TKIs do not Enhance Tumor Growth when Combined with Fractionated IR

Figure 5B:
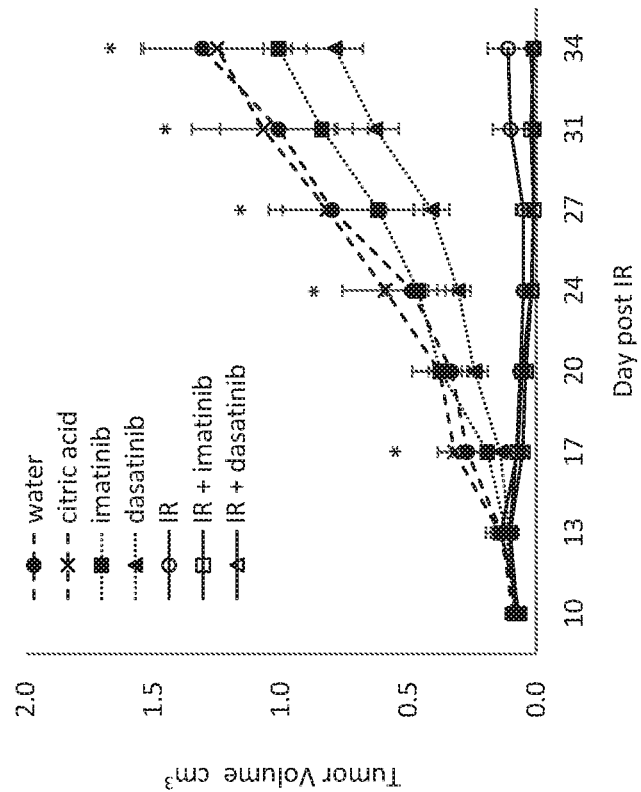
FIGS. 5A and 5B demonstrate that TKIs preserve salivary gland function without promoting tumor growth in a fractionated IR model. Mice were treated with imatinib (pre/post) relative to each fraction of IR (4 Gy) over 5 consecutive days. Saliva was collected prior to IR (day 0) and at 60 days after IR as described in Examples. Saliva production (saliva weight/animal weight) for each cohort of mice was normalized against the production for vehicle treated mice to generate the data shown (FIG. 5A). Data shown represents the average plus S.E.M. (error bars) (n>3). *=p<0.01 for saliva collected from radiated mice compared to vehicle treated mice. ***=p<0.05 for saliva collected from mice treated with IR plus Imatinib compared to mice given IR alone. Nude mice were injected with $4 \times 10^6$ log-phase FaDu cells. From days 10-14, mice received fractionated IR (5×6 Gy) with or without the pre/post treatment with either dasatinib or imatinib. Tumor volume was measured twice a week over the course of the experiment. On day 34 final measurements were collected (FIG. 5B). The data represent the average tumor size plus the S.E.M. (error bars) (n>7). *=p<0.05 for tumors in mice treated with dasatinib alone compared to citric acid alone (vehicle).
Figure 5A:
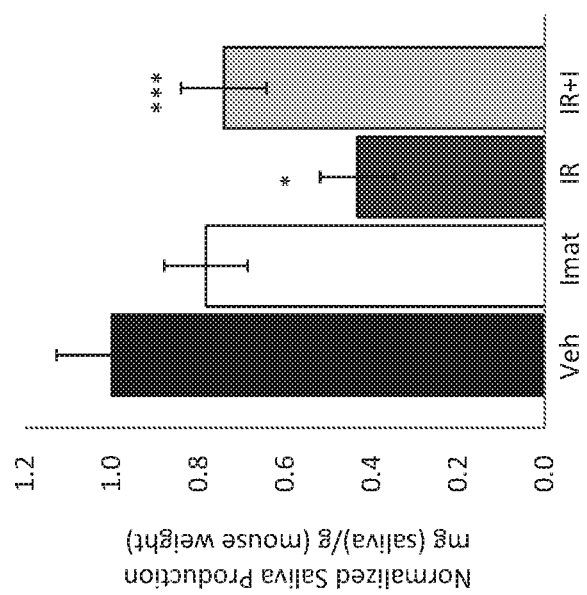

IR is typically delivered to patients in multiple fractions over 4-6 weeks. To assess the impact of TKIs on salivary gland function under similar conditions, we used a fractionated model wherein mice received 4 Gy IR to the head and neck on each of 5 consecutive days. Mice were dosed with imatinib before and after (pre/post) each fraction of IR. As shown in FIG. 5A, in mice treated with IR alone, saliva production was reduced by 60% compared to the vehicle control group. However, in mice treated with IR plus imatinib, salivary gland function at 60 days after IR was not significantly different from the vehicle treatment alone, or imatinib only control groups, indicating that imatinib can provide protection of salivary gland function in a fractionated IR model. We next asked if TKIs impact the growth of HNSCC tumor xenografts when delivered in combination with fractionated IR. FaDu cells were grown as flank xenograft tumors and mice were given 6 Gy of IR at the tumor site for 5 consecutive days.

FaDu cells (4×106) were suspended in 0.9% NaCl and injected subcutaneously into the right flank of nude mice. Mice were kept in a pathogen-free environment, and xenografts were measured by micro-caliper twice a week. When tumors reached 0.07 cubic cm, mice were sorted by tumor size and randomized into the corresponding treatment groups. Dasatinib (20 mg/kg) and imatinib (50 mg/kg) were given following the pre/post regimen relative to each fraction of IR. Tumor volume was calculated using the equation width$^2$×length)/2. Mice were sacrificed when tumors reached 2.0 cubic cm.

Before and after each IR treatment, mice were dosed with either imatinib or dasatinib (pre/post dosing). Fractionated IR alone resulted in the attenuated growth of FaDu derived xenograft tumors (FIG. 5B), and the addition of either dasatinib or imatinib had no effect on tumor growth. Interestingly, in mice treated with either dasatinib or imatinib alone there was a trend towards reduced tumor growth compared to their respective controls. Together, these data demonstrate that PKC-delta inhibition is effective in protecting salivary gland function without sacrificing the cytotoxic effect of IR on HNC, and support evaluation of TKIs for radioprotection of the salivary gland in patients receiving IR for HNC.

Example 6

TKIs Increase the Proliferation/Regeneration of Salivary Gland Cells after Fractionated IR C57/B16 mice are treated with 4 Gy IR to the head and neck on each of five consecutive days. Imatinib (50 mg/kg in water) is delivered by oral gavage 1 hour prior and 3 hours post IR, plus twice a week for the duration of the experiment. In addition to imatinib combined with IR, control groups will include vehicle alone, IR alone, and imatinib alone. Using a one-way ANOVA study, a sample size of 5 in each of the 4 groups is used to achieve 92% power using an F test with a 0.05 significance level. 20 mice are used per time point, or 180 mice for the entire experiment. Salivary flow is assayed prior to the start of the experiment (time=0) and at 2, 7, 14, 30, 60, 90, 120, and 150 days after IR. Five mice from each group will be sacrificed at each time point and the salivary glands removed and processed for histology. For analysis of cells in S phase, mice are injected with BrdU one hour prior to sacrificing. IHC staining for BrdU, active caspase-3 and Ki67 is performed as previously described (Nguyen HM1, Reyland M E, Barlow L A., Mechanisms of taste bud cell loss after head and neck irradiation. J Neurosci. 2012 Mar. 7; 32(10):3474-84). Changes in the cell cycle markers cyclin D1 (G1), pH3 (mitosis) are also analyzed. Tissues are stained with anti-AQPN5, counterstained with hematoxylin, and acinar cell number is quantified using Aperio software. Ductal cells, which can be derived from the Aperio data as the non-AQPN5 staining fraction, or directly by using a number of ductal cell makers (Marmary, Y., et al., Radiation-Induced Loss of Salivary Gland Function Is Driven by Cellular Senescence and Prevented by IL6 Modulation. Cancer Res. 2016; 76(5):1170-80), are also quantified. Mouse salivary gland tissues are analyzed by a board certified veterinary pathologist. The results indicate that TKIs increase the proliferation/regeneration of salivary gland cells after administration of fractionated IR.

The foregoing examples of the present invention have been presented for purposes of illustration and description. These examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

What is claimed is:

1. A method for regenerating non-cancerous cells following treatment of a cancer patient, the method comprising administering a therapeutically effective amount of a tyrosine kinase inhibitor (TKI) for several months after administering a cancer treatment to the cancer patient.

2. The method of claim 1, wherein the cancer treatment comprises radiation therapy.

3. The method of claim 1, wherein the TKI inhibits at least one of Protein Kinase C-delta, c-Abl, and Src-family kinase.

4. The method of claim 1, wherein the TKI inhibits a non-receptor tyrosine kinase.

5. The method of claim 1, wherein the TKI is selected from the group consisting of bosutinib, dasatinib, imatinib, nilotinib, pazopanib, ponatinib, sunitinib, and combinations thereof.

6. The method of claim 2, wherein the TKI administration begins prior to or concurrent with radiation therapy and continues at least twice weekly for at least 90 days following a single dose of irradiation.

7. The method of claim 6, further comprising administration of the TKI at least twice weekly for 150 days following a single dose of irradiation.

8. The method of claim 1, wherein the non-cancerous cells are salivary gland acinar cells.

\* \* \* \* \*